US00PP26155P2

(12) United States Plant Patent
Roebuck

(10) Patent No.: US PP26,155 P2
(45) Date of Patent: Nov. 24, 2015

(54) ***AGAPANTHUS* PLANT NAMED 'GOLDEN DROP'**

(50) Latin Name: ***Agapanthus* hybrid**
Varietal Denomination: Golden Drop

(71) Applicant: Christopher Gardiner Roebuck, Auckland (NZ)

(72) Inventor: Christopher Gardiner Roebuck, Auckland (NZ)

(73) Assignee: HORTEX TREES AND SHRUBS, LTD., Aukland (NZ)

( * ) Notice: Subject to any disclaimer, the term of this patent is extended or adjusted under 35 U.S.C. 154(b) by 142 days.

(21) Appl. No.: 13/987,574

(22) Filed: Aug. 9, 2013

(51) Int. Cl.
*A01H 5/00* (2006.01)

(52) U.S. Cl.
USPC ..... Plt./398

(58) Field of Classification Search
USPC ..... Plt./398
CPC ..... A01H 5/0272; A01H 5/0205
See application file for complete search history.

(56) References Cited

PUBLICATIONS

Growell Plants, retrieved from Google search on Jan. 7, 2015.*

* cited by examiner

*Primary Examiner* — Keith O. Robinson
(74) *Attorney, Agent, or Firm* — Penny J. Aguirre

(57) ABSTRACT

A new cultivar of *Agapanthus* named 'Golden Drop', characterized by its variegated foliage with light green centers and creamy yellow margins, and its flowers that are light blue in color and held on erect stems.

2 Drawing Sheets

Botanical classification: *Agapanthus* hybrid.
Varietal denomination: 'Golden Drop'.

BACKGROUND OF THE INVENTION

The present invention relates to a new and distinct cultivar of *Agapanthus* of hybrid origin and will be referred to hereafter by its cultivar name, 'Golden Drop'. 'Golden Drop' represents a new perennial herb grown for landscape use.

The Inventor discovered the new cultivar in September of 2004 as a naturally occurring chimeral mutation of *Agapanthus* 'Streamline' (not patented) that was growing in a container at his nursery in Auckland, New Zealand.

Asexual propagation of the new cultivar was first accomplished by division by the Inventor in December of 2005 in Auckland, New Zealand. Asexual propagation by division has determined that the characteristics of this cultivar are stable and are reproduced true to type in successive generations.

SUMMARY OF THE INVENTION

The following traits have been repeatedly observed and represent the characteristics of the new cultivar. The characteristics in combination distinguish 'Golden Drop' as a distinct cultivar of *Agapanthus*.

1. 'Golden Drop' exhibits variegated foliage with light green centers and creamy yellow margins.
2. 'Golden Drop' exhibits flowers that are light blue in color and held on erect stems.

The parent plant of 'Golden Drop', 'Streamline', differs from 'Golden Drop' in having green non variegated foliage. 'Golden Drop' can be most closely compared to the cultivars 'Tinkerbell' (not patented) and 'Gold Strike' (U.S. Plant Pat. No. 20,650). Both are similar to 'Golden Drop' in having variegated foliage. 'Tinkerbell' differs from 'Golden Drop' in having foliage with green centers and white margins and in having flowers that are darker blue in color (medium blue). 'Gold Strike' differs from 'Golden Drop' in having foliage with darker green centers and golden yellow margins.

BRIEF DESCRIPTION OF THE DRAWINGS

The accompanying colored photographs illustrate the overall appearance and distinct characteristics of the new *Agapanthus*. The photographs were taken a one year-old plant of 'Golden Drop' as grown outdoors in a 9-cm container in Boskoop, the Netherlands.

The photograph in FIG. 1 provides a view of a plant of 'Golden Drop' in bloom.

Figure 1:
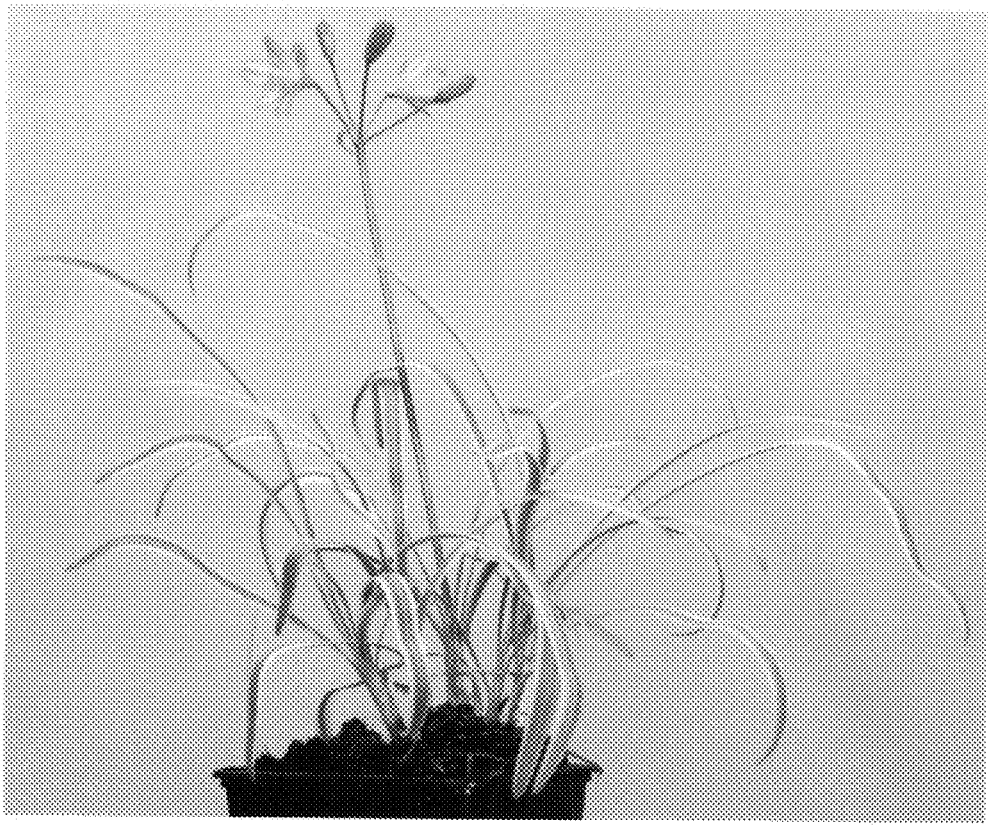
Figure 2:
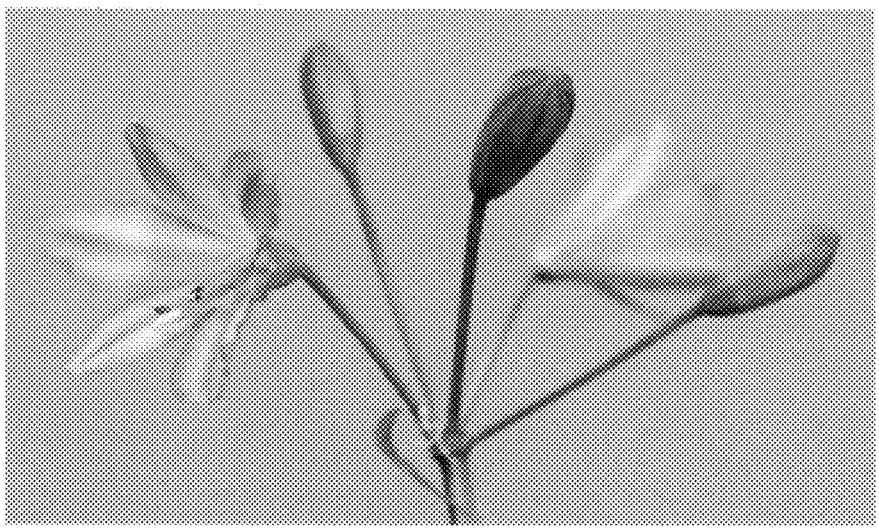

The photograph in FIG. 2 provides a close-up view of an inflorescence of 'Golden Drop'.

Figure 3:
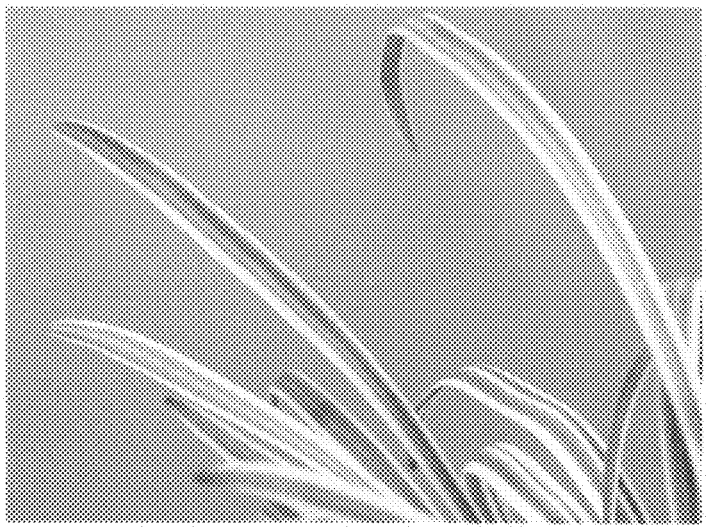

The photograph in FIG. 3 provides a close-up view of the foliage of 'Golden Drop'.

The colors in the photographs are as close as possible with the photographic and printing technology utilized and color values cited in the detailed botanical description accurately describe the colors of the new *Agapanthus*.

DETAILED BOTANICAL DESCRIPTION

The general observations and descriptions describe one year-old plants of 'Golden Drop' as grown outdoors in 9-cm containers in Boskoop, the Netherlands. The phenotype of the new cultivar may vary with variations in environmental, climatic, and cultural conditions, as it has not been tested under all possible environmental conditions. The color determinations are in accordance with The 2007 R.H.S. Colour Chart of The Royal Horticultural Society, London, England, except where general color terms of ordinary dictionary significance are used.

General description:

*Blooming period.*—Blooms from late June into August in New Zealand.

*Plant type.*—Herbaceous perennial herb.

*Plant habit.*—Upright with cascading foliage.

*Height and spread.*—Average of 23.8 in height and 20.9 cm in spread in a 9-cm container, a two year-old plant reaches about 50 cm in height and spread.

*Cold hardiness.*—At least to U.S.D.A. Zone 8.

*Diseases and pests.*—No susceptibility or resistance to diseases or pests has been observed.

*Root description.*—Fleshy main roots and fibrous secondary roots, color 156D.

*Propagation.*—Division.

*Growth rate.*—Low.

Foliage description:

*Leaf shape.*—Ligulate and moderately recurved.

*Leaf division.*—Simple.

*Leaf base.*—Cuneate.

*Leaf arrangement.*—Distichous.

*Leaf apex.*—Acute.

*Leaf aspect.*—Emerging leaves erect, then cascade.

*Leaf density.*—Medium to sparse.

*Leaf venation.*—Parallel, upper surface; 148D, lower surface; 143C.

*Leaf margins.*—Entire.

*Leaf size.*—Average of 20.4 cm in length and 0.9 cm in width.

*Leaf surface.*—Both surfaces smooth and slightly leathery, upper surface slightly glossy, lower surface very slightly glossy.

*Leaf number.*—Average of 6 leaf blades per rosette (24 per plant).

*Leaf color.*—Young leaves, upper surface; 144B, margined and striped ranging between 154C and 3C, young leaves, lower surface; 144C, margined and striped ranging between 154C to 154D and 3C, mature leaves, upper surface; 146B, striped 148D, margined 150D, mature leaves, lower surface; 148D, margined 154D, variegation is strongly persistent.

*Leaf attachment.*—Sessile.

Flower description:

*Inflorescence type.*—Simple umbel, the opening of the inflorescence bract is on one side.

*Flower fragrance.*—None.

*Flower type.*—Rotate, campanulate in shape, base of tepals fused.

*Flower number.*—Average of 3 flowers per lateral stem.

*Inflorescence size.*—Average of 4.3 cm in depth and 7.8 cm in diameter.

*Flower size.*—About 2.5 cm in depth and 2.7 cm in diameter.

*Lastingness of inflorescence.*—Average 7 days.

*Flower aspect.*—Outward.

*Peduncle.*—Strong, 1 per rosette (up to 4 per plant in a one gallon container), slightly elliptic, held at 10°, average of 17.7 cm in length and 0.3 cm in width at distal region and 0.25 cm in width at proximal region, color is 147D to 148D, striped between 151D and 3C, smooth and glabrous surface.

*Pedicels.*—Strong, average of 2.6 cm in length and 1 mm in width, held erect to outward, color 148A, smooth and glabrous surface.

*Flower buds.*—Obovate in shape, average of 1.5 cm in length and 5 mm in width, color 93B, base 91B and 92B, smooth and glabrous surface.

*Tepals.*—6 (3 inner and 3 outer), narrow obovate in shape, margins; outer tepals entire, inner tepals slightly wavy, both surfaces are smooth, apex; inner tepals obtuse, outer tepals broad acute, inner and outer tepals (perianth) an average of 2.7 cm in length with the lower 50% fused into the perianth tube (1.25 cm in length), inner tepals 0.9 cm in width, outer tepals 0.7 cm in width, perianth 2.7 cm in width, color when opening upper surface; 91D, at the perianth tube, top and margins the central stripe is 92B, color when opening outer surface; 92A, perianth tube is 92B, color when fully open upper surface; 91D at the perianth tube, top and margins, striped 92B, color when fully open lower surface; 92A, perianth tube 92B, fading to 94C.

Reproductive organs:

*Gynoecium.*—1 pistil, average of 1.5 cm in length, stigma is narrow clavate in shape and 92A in color, style is 1.45 cm in length and 91B fading towards the base and becoming NN155D in color, ovary is 4C in color.

*Androcoecium.*—6 stamens, anthers are dorsified, oblong in shape, average of 3 mm in length, and 202B in color, filament is 1.5 cm in length and 91B, fading for base and becoming NN155D, pollen is moderate in quantity and 13A in color.

*Fruit/seed.*—Have not been observed.

It is claimed:

1. A new and distinct cultivar of *Agapanthus* plant named 'Golden Drop' as herein illustrated and described.

* * * * *